United States Patent [19]

Palermo et al.

[11] Patent Number: 4,644,573
[45] Date of Patent: Feb. 17, 1987

[54] COMPUTED TOMOGRAPHY METHOD AND APPARATUS

[75] Inventors: Anthony Palermo, South Euclid; Anton Z. Zupancic, Kirtland, both of Ohio

[73] Assignee: Picker Corporation, Cleveland, Ohio

[21] Appl. No.: 226,203

[22] Filed: Jan. 19, 1981

Related U.S. Application Data

[63] Continuation of Ser. No. 76,193, Sep. 17, 1979.

[51] Int. Cl.$^4$ .............................................. G03B 41/16
[52] U.S. Cl. .......................................... 378/15; 378/17
[58] Field of Search ....................... 250/445 T; 378/15

[56] References Cited

U.S. PATENT DOCUMENTS

| | | | |
|---|---|---|---|
| 4,063,792 | 12/1977 | Lodge | 250/445 T |
| 4,093,859 | 6/1978 | Davis | 250/445 T |
| 4,137,455 | 1/1979 | Fetter | 250/445 T |

Primary Examiner—Craig E. Church
Attorney, Agent, or Firm—Watts, Hoffmann, Fisher & Heinke Co.

[57] ABSTRACT

Apparatus is disclosed for providing electrical energy to orbital components of a computed tomography (CT) scanning unit. The apparatus includes a number of high voltage slip rings immersed in an insulating dielectric material. Each slip ring contacts a stationary brush biased to contact the slip ring to insure maintenance of a low resistance path between a stationary source of high potential and a cathode and anode pair of an orbital X-ray tube. A number of low voltage slip rings are further included to facilitate transmission of low voltages to other orbital components of the CT unit. The apparatus is of a compact light-weight design and is mounted to tilt certain components about an axis which intersects a patient's torso to provide CT scanning flexibility.

9 Claims, 9 Drawing Figures

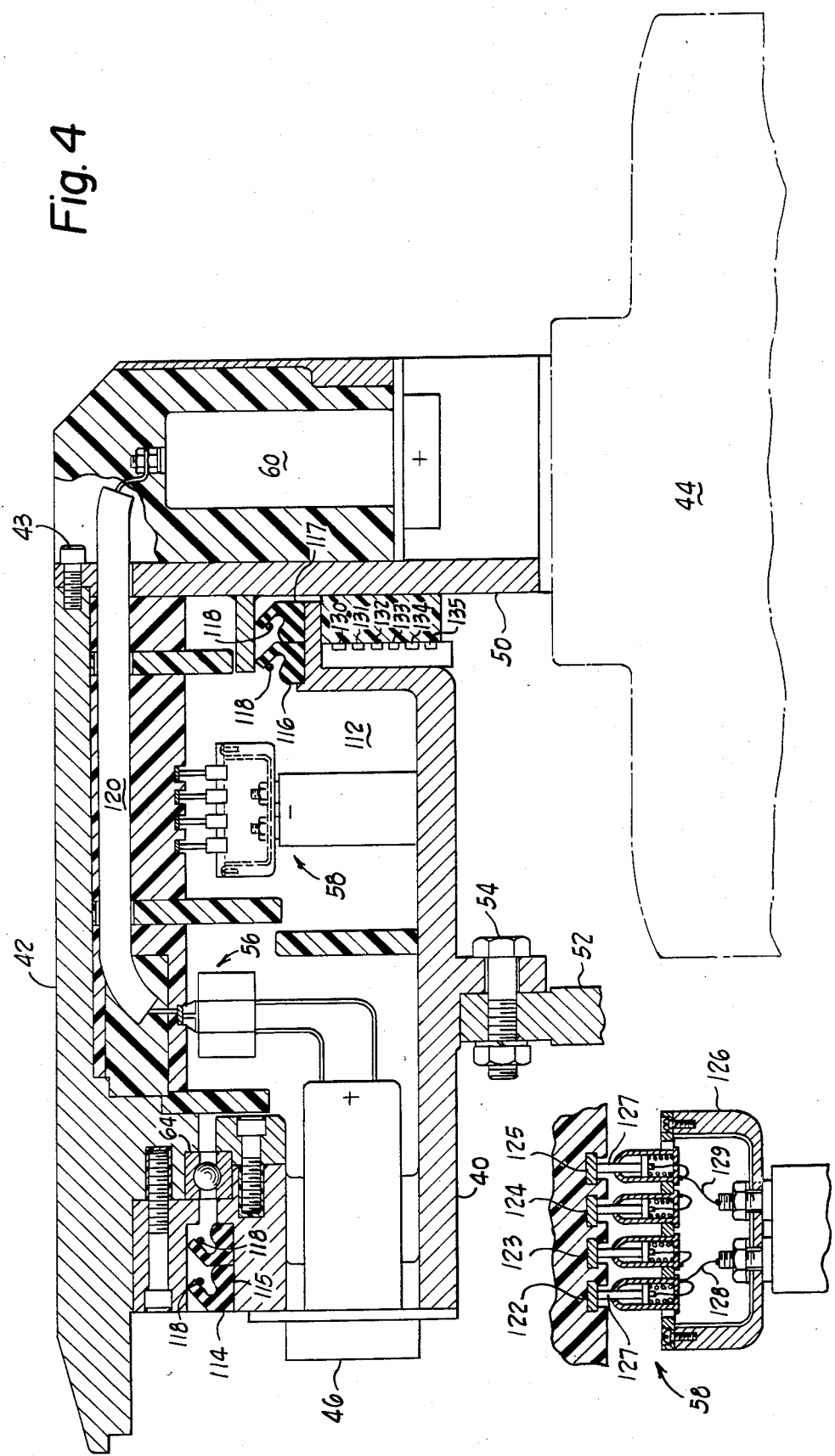

COMPUTED TOMOGRAPHY METHOD AND APPARATUS

This is a continuation of application Ser. No. 76,193 filed Sept. 17, 1979.

BACKGROUND OF THE INVENTION

1. Field of the Invention

The invention relates to an improved apparatus for supplying electrical power to orbital elements of a computed tomography scanning unit.

2. Prior Art

The art of computed tomography (CT) scanning has greatly improved a physician's ability to acurately diagnose the internal structure of a patient. The process of CT scanning involves the sending of X radiation through a patient from a variety of different locations, and determining the intensity of the transmitted radiation with one or more X-ray detectors. Intensity data is sent to imaging electronics for image reconstruction. In many studies, the image viewed by the doctor presents greater detail than conventional X-ray techniques and therefore can be better used to diagnose the patient's condition.

In a typical computed tomography scanning environment, an X-ray source is orbited about a patient while the patient is irradiated. The detector or detectors either orbit with the source or form a non orbiting array of detecting units. In either configuration a substantial amount of X-ray emitting and shaping apparatus rotates with the X-ray source. This apparatus as well as the X-ray source must be powered by electrical energy supplied from a source exterior to the rotating CT apparatus.

One particular computed tomography scanning unit includes an orbiting source of X radiation which emits an X-ray beam in a spread configuration. The detector units are stationary relative to the X-ray source and form an annular ring of detectors about the patient. The X radiation source is positioned to transmit X-rays through the patient along a series of beam paths as it is orbited. Since a variety of beam generating, shaping and transmitting functions must be performed on the orbiting apparatus as orbiting occurs, a number of electrical signals must be supplied to this apparatus.

To create X-radiation, a large potential difference on the order of 150 kilovolts must be provided. This voltage is used to accelerate electrons from an X-ray tube cathode to an anode for X radiation generation. Typically a filament voltage and an X-ray focusing cup control are required so that a number of high voltage inputs are necessary. Providing these high voltage potential differences to the X radiation source creates design problems which have in the past required sophisticated cabling and input techniques.

A number of low voltage control and energization signals must also be transmitted to the orbiting apparatus. It is known that the X-ray tube tends to heat up due to the collisions of the accelerated electrons with the X-ray anode and to dissipate the heat build up some CT units require that the X-ray anode be continuously rotated. A motor, which typically requires at least two and possibly three leads, provides this rotational cooling.

In order that the beam produced by the X radiation tube occupies the proper dimensions, it is necessary that the X radiation be collimated. A collimator is therefore mounted to orbit with the x-ray tube. The collimator includes an adjustment motor which is powered by an external source of energy.

Control solenoids and a laser source to aid in patient positioning also orbit the patient and receive power from a stationary power source. Actuation of the solenoids is achieved via command signals which are also transmitted to the orbiting apparatus. Since these various functions must be coordinated to produce the proper X-ray transmission and shaping, a clocking signal must also be sent to the orbiting apparatus.

Although most of the detectors on the described CT apparatus are stationary, one orbiting detector is included which is used to calibrate the X radiation and provide a reference signal. This orbiting detector requires energization from a stationary source and provides an output signal which must also pass through cabling which leads from the orbiting apparatus to CT imaging electronics.

Present state of the art CT scanning units provide requisite cabling inputs to the rotating portions of the CT unit through rather sophisticated cable takeup mechanisms. One such mechanism is disclosed in patent application Ser. No. 917,068 filed, June 19, 1978, and entitled "Computed Tomography Method and Apparatus" which has been assigned to the Picker Corporation. Although this cable takeup mechanism presents an advantage over other power input mechanisms, it is limited in its applicability by certain design disadvantages.

Apparatus disclosed in the referenced cable take up patent application includes a flexible cable of finite length which is wound and unwound from a mandrel as the CT unit causes the X-ray tube to orbit. A CT unit employing such a mechanism can only be rotated a finite amount before its direction of rotation must be reversed. Such a reversal in direction introduces a complexity in controlling the rotation of the CT unit.

A certain amount of power is expended in moving the cable during CT unit rotation. This added power expenditure limits scanning speed and may add a nonuniformity of rotation during an X-ray exposure.

Maintenance of the cables is perhaps the most disadvantageous feature of the cable takeup energization method. Constant flexing of the cable even with the take up mechanism of the referenced application may eventually cause it to crack or break so that it must periodically be replaced.

To overcome some disadvantages noted with regards to the cable takeup mechanisms, a slip ring type of power transferral has been suggested. The suggested slip ring arrangement, however, has not completely solved the problems inherent with prior mechanisms and may not adequately insulate the high voltage potentials required for CT scanning. The arrangement discloses only one slip ring for providing power while from the above it is apparent that a number of high power inputs are necessary.

More CT scanning information is available if the plane in which the patient lies can be tilted with respect to the X-ray beam plane. Due to the size and configuration of prior art CT slip rings, the examination of the patient and the orbital axis could not be changed relatively. Thus, additional information was available only if the patient were shifted laterally with respect to the X-ray beam plane. It is therefore apparent that suggested slip ring power arrangements have inadequately dealt with the power transmittal problems in prior art cable take up mechanisms.

SUMMARY OF THE INVENTION

The present invention provides a unified, compact, slip-ring arrangement for transmitting electrical energy to orbiting components in a CT scanning unit. The slip-ring arrangement is completely immersed in an insulating fluid to insulate the high X-ray generating voltages from the rest of the unit. A plurality of both high and low voltage slip rings are provided to generate, calibrate and shape the X radiation.

One embodiment of the invention includes a stationary gantry apparatus to which an orbiting assembly is mounted for orbital rotation about a scanning axis coincident with a patient axis. An X-ray source powered by a high voltage input is attached to the assembly and irradiates a patient for reconstruction imaging. The source generates X radiation which is collimated into beams before traversing the patient. The radiation impinges upon an array of X-ray detectors which can either be non orbital or movable with the source.

Both high and low electrical potential is provided to the rotating assembly by the present design. A high voltage input receptacle is mounted to the gantry for receiving a high electrical input. The high electrical input is transmitted to the orbitally rotating portion of the assembly by means of a connection technique which includes spring loaded brushes attached to the orbitally stationary gantry and a number of annularly shaped slip-rings attached to the rotating assembly. The brushes are maintained in contact with the slip rings to insure there exists a low resistance path from the input receptacle to the rotating assembly. Attached to the slip ring is a transmission line for coupling the high input potential to the X-ray source. By means of this arrangement, a high electrical potential is transmitted to the orbiting X-ray source without the use of a complex cable takeup arrangement.

In the preferred embodiment of the invention, a number of high voltage rotating slip rings are electrically coupled via brushes to stationary high voltage input receptacles. Multiple focus X-ray tubes with grid potential control require multiple high potential voltage inputs so that apparatus embodying the invention utilizes four orbitally rotating high voltage slip rings. The apparatus further includes a plurality of low input slip rings for transmitting low input voltages from the stationary gantry to the orbiting assembly. This configuration provides the CT user significant design flexibility in sending power and control signals to the orbiting assembly.

In this embodiment the orbiting and nonrotating portions of the CT scanning unit are configured to define a cavity surrounding the high voltage input slip rings. This cavity is filled with an insulating dielectric fluid which completely surrounds the high voltage slip ring and brush arrangement to effectively insulate the high potential passing through the slip ring from the rest of the CT unit. In this way arcing from the high potential slip ring to electrical ground does not occur. Seals are provided to prevent leakage of the dielectric fluid from the CT unit thereby maintaining the insulating fluid in contact with the entire slip ring. Only the high potential slip ring arrangements are insulated since the low potential slip rings carry low power current and present no arcing danger.

The length along the axial dimension of the CT unit embodying the improved high voltage slip-ring arrangement is short. This compact design allows the unit to be tilted about an axis transverse to the scanning axis by approximately 20° and allows the patient to be scanned in planes other than a vertical cross section.

From the above, it is apparent that one feature and object of the present invention is to provide a simplified, compact and safely insulated brush and slip-ring arrangement for providing both high and low power to orbiting components of a CT scanning unit. A second advantage of the invention is to provide a number of slip-rings thereby providing CT unit design flexibility. The compact nature of the apparatus allows the slip-ring arrangement to be tilted so the orbiting X-ray tube can transmit radiation across non-vertical cross sections.

These and other features and advantages of the invention will become more apparent as the invention becomes better understood from the detailed description that follows, when considered in conjunction with the accompanying drawings.

BRIEF DESCRIPTION OF THE DRAWINGS

FIG. 4 is an enlarged cross sectional view of a portion of the scanner shown in FIG. 3B.

FIG. 4A shows a further enlarged part of the cross sectional portion shown in FIG. 4.

DESCRIPTION OF THE PREFERRED EMBODIMENT

Figure 1:
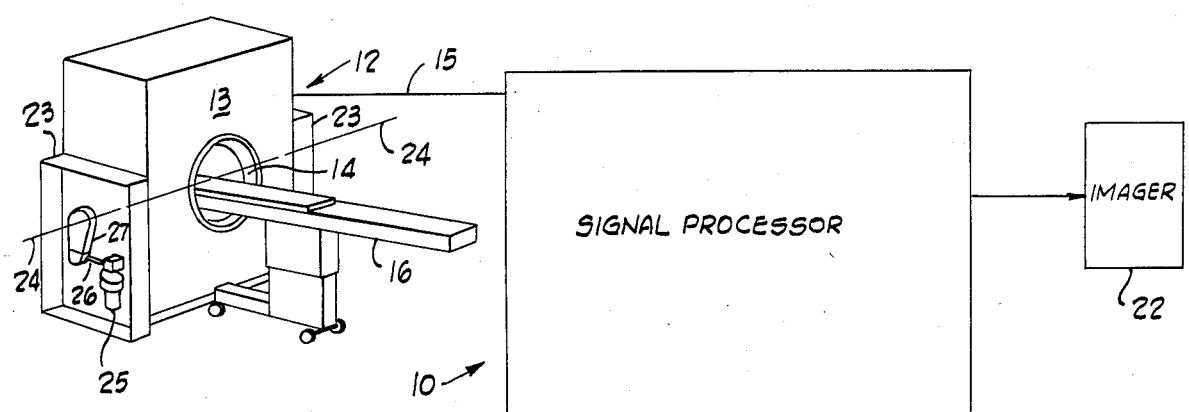
FIG. 1 shows schematically the elements comprising a CT scanning arrangement.

Referring now to the drawings and FIG. 1 in particular, a computed tomography system 10 designed for examining the internal structure of a patient is shown. The system comprises a scanning unit 12, a couch 16, a signal processor 20, and imager 22. The scanning unit includes a housing 13 which covers the X-ray apparatus and provides an attractive appearance to the unit. Before a CT scan the couch 16 and a patient lying on the couch are moved into an aperture 14 in the housing 13. An X-ray tube within the unit is energized and transmits X radiation, thereby irradiating the patient.

The scanning unit 12 can be tilted about an axis 24 parallel to the floor. This movement provides a flexibility in scanning without repositioning of the patient. Two support columns 23 mount the unit 12 for rotation about the axis 24. Rotational motion is applied by an AC motor 25, a right angle drive 26, and a pivot arm 27.

A series of X-ray detectors detect X-ray intensity after it passes through the patient and produce electrical signals in response to the radiation. These electronic signals representing patient densities are sent from the scanning unit to the signal processor 20 by an electrical connection 15. The signal processor receives these signals and utilizes known CT processing techniques to produce signals representing the variations in patient density across a patient cross section. The signal processor then sends signals to an imager 22 which provides an image of the patient.

Figure 2:
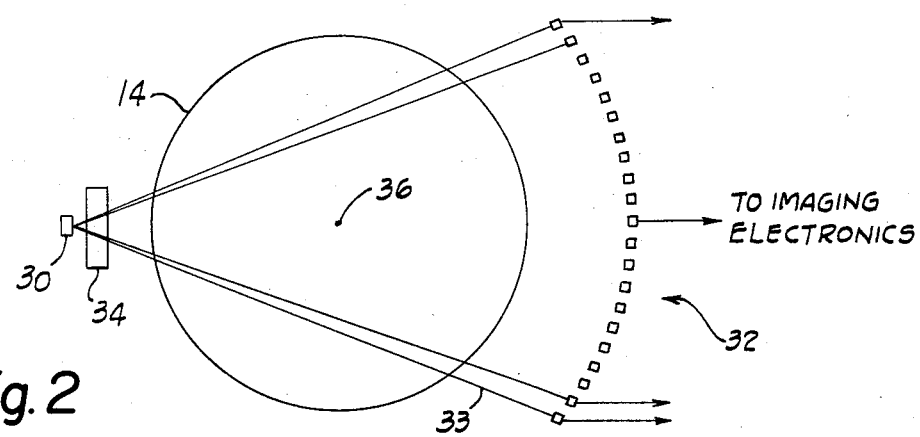
FIG. 2 schematically shows a source of X-rays positioned to irradiate a patient cross section.

FIG. 2 schematically illustrates a CT X-ray source 30 and array of detectors 32 positioned about the patient aperture 14. The source 30 emits a spread of X radiation which passes through a collimator 34 which shapes the X radiation into a number of individual beams. One X-ray beam 33 is shown as it passes through the patient aperture and impinges upon a detector in the circular array 32 of X radiation detectors. The illustrated detectors are shown positioned on the side of the patient aperture opposed from the source 30 and therefore certain of them detect radiation intensity after that radiation has passed through the patient.

Although the FIG. 2 illustration shows a finite number of detectors, so called "stationary detector" CT designs provide an array of detectors which completely surround the patient aperture. Thus, it is possible for the X radiation detectors to remain stationary while the X radiation source 30 orbits about the patient aperture irradiating the patient from a number of different positions. The detectors are of a known design and convert X radiation into an electrical signal whose outputs can be sent to the signal processor 20 for CT image formation.

All CT reconstruction algorithims require that the X radiation impinge upon the patient cross section from a number of different positions so that intensity data from radiation originating from various positions is obtained. By obtaining this multi-position intensity data it is possible to reconstruct a mapping or image of the density variations within the patient cross section. To achieve this multi-position irradiation the present invention includes a rotating assembly which supports the X-ray source 30 and is movable relative to the X-ray detector array 32.

Movement of the X-ray source in a circular path causes electrical energization problems which are compounded by the high voltage potential differences coupled to the X-ray tube.

Figure 3B:
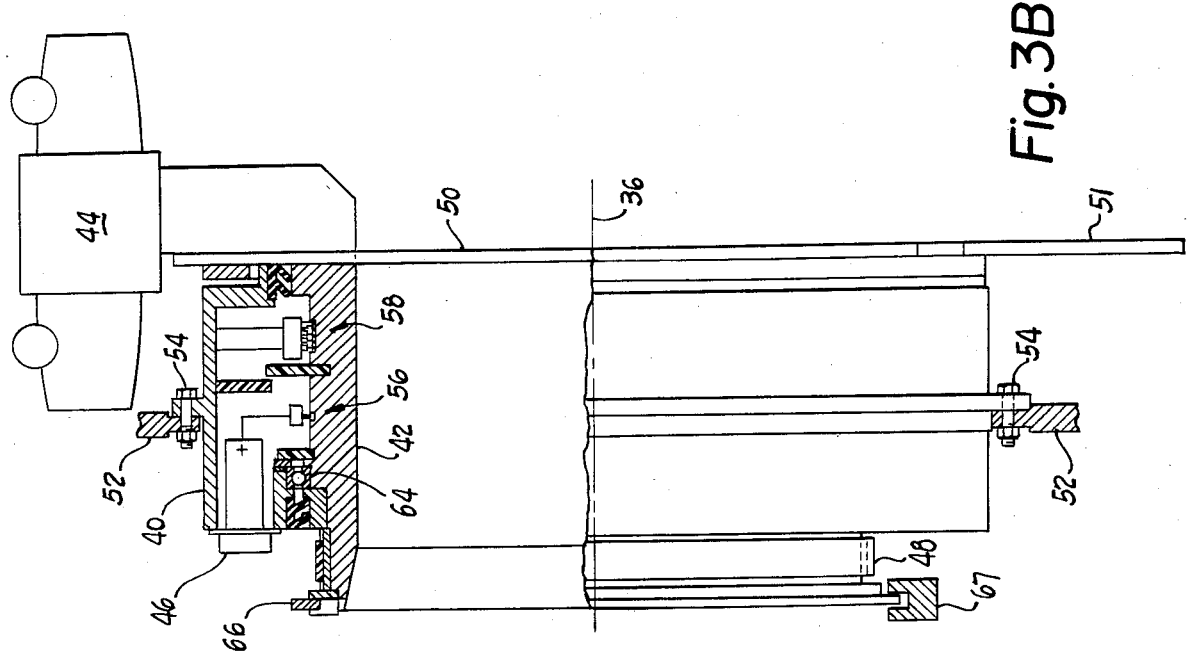
FIG. 3B shows a partially sectioned view of the CT scanner shown in FIG. 3A.
Figure 3A:
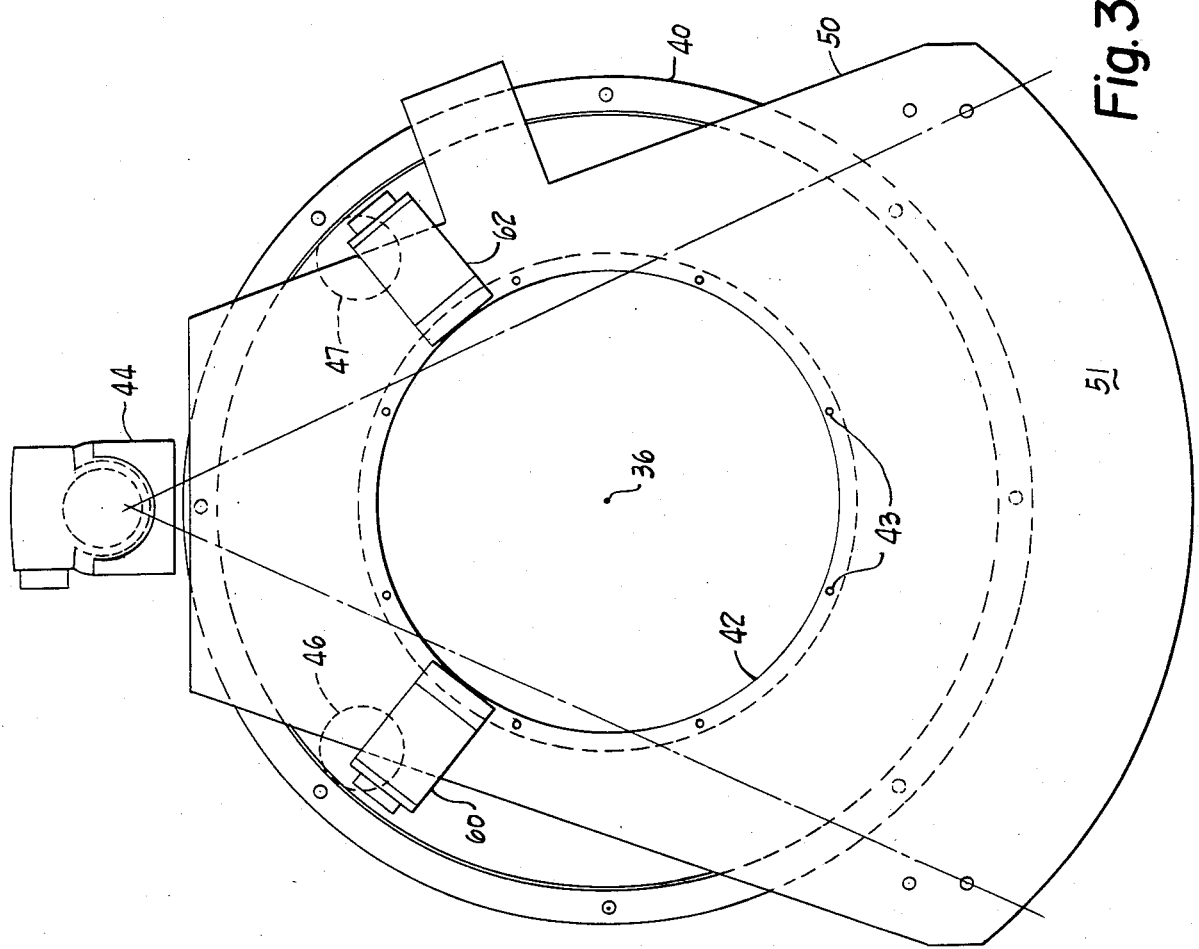
FIG. 3A shows a front elevational view of elements of a CT scanner.

FIGS. 3A and 3B illustrate a new and improved CT apparatus which facilitates the sending of potential differences to the X-ray source for X-ray generation. The CT apparatus shown includes a stationary gantry arrangement 40, a rotating assembly 42 and an X-ray tube housing 44. During operation a belt drive 48 causes the rotating assembly 42 to rotate within the stationary gantry 40 thereby irradiating a patient cross section of interest from a number of different positions. The rotating assembly comprises a frame 50 attached to an annular portion of the assembly by eight connectors 43 (See FIG. 3A) spaced evenly about the patient aperture 14. The frame 50 carries the X-ray housing 44 for orbital rotation about the patient aperture 14.

One aspect of the invention is the provision of high potential differences to the cathode and anode of the X-ray tube. In one embodiment of the invention the potential difference between cathode and anode is on the order of 150,000 volts. This potential difference is provided by a positive and negative input each on the order of 75,000 volts removed from ground. To transmit electrical energy to the X-ray tube the stationary gantry 40 includes both a positive 46 and negative 47 high voltage electrical receptacle or connector. The positive voltage receptacle 46 shown in FIG. 3B receives a voltage input of plus 75,000 volts from an external voltage source. The negative high voltage receptacle (not shown in FIG. 3B) receives an input voltage of approximately 75,000 negative volts.

The assembly further comprises a positive 56 and negative 58 slip ring portion which receive these high voltage inputs and transmit a high voltage differential from the stationary gantry portion 40 to the rotating assembly 42 for transmittal to the X-ray tube. The first positive portion 56 includes only one slip ring which is coupled to the positive receptacle 46. The second negative portion 58 includes four slip rings and is designed to receive more than one negative high voltage input. The purpose of this multiplicity in high voltage slip ring configuration is to allow control of the X radiation generation by utilization of either multiple focus or grid potential voltage inputs.

After the high voltage potential is transmitted to the rotating assembly 42 it is further transmitted along cabling (shown in FIG. 4 as reference numeral 120) to two high voltage receptacles 60, 62 mounted to the frame 50. A first receptacle 60 receives the positive voltage and a second receptacle 62 receives the negative high voltage potential inputs. From these receptacles the high voltage is transmitted to the anode (positive) and cathode (negative) of the rotating X-ray tube.

The gantry is attached to a support 52 radially removed from the patient aperture by means of suitable connectors 54 such as a nut and bolt arrangement. This mounting serves to maintain the stationary gantry 40 in position while allowing the support 52 to be tilted about an axis perpendicular to the axis of CT scanning 36. If the support 52 is tilted while the patient maintained in a horizontal position the X radiation will traverse the patient aperture at a non vertical angle and thereby provide flexibility in CT scanning. If, for example, the support 52 is tilted 20° about an axis perpendicular to the scan axis 36 the cross section of patient irradiation will also be tilted 20° to the vertical.

The geometrical configuration of the frame 50 and X-ray housing 44 is such that the rotating assembly 42 is well balanced about the scan axis 36. The frame 50 is much wider at a side 51 opposed from the X-ray housing and this width counterbalances the weight of the X-ray housing and enclosed tube and provides a symmetrical mass distribution about the axis 36.

The stationary gantry 40 supports the rotating assembly 42 along an annular bearing connection 64, which allows free orbital rotation of the assembly 42 about the axis 36. The compact design of the apparatus allows one bearing to provide sufficient support to the rotating assembly.

It is important in CT scanning that the position of the X-ray tube be precisely known during all times of an X-ray exposure. For this reason, an encoder 66 in the form of an annular ring is attached to the rotating assembly 42. This encoder 66 includes a number of marks equally spaced about the ring which indicate the angular orientation of the encoder. As the annular ring moves about the center axis an optical encoder 67 determines the position of the ring relative to the stationary gantry 40. In this way the precise position of the X-ray source can be determined at all times during irradiation of the patient. This position data is correlated with intensity readings from the X-ray detector array and utilized in reconstruction algorithms known within the art.

Figure 5A:
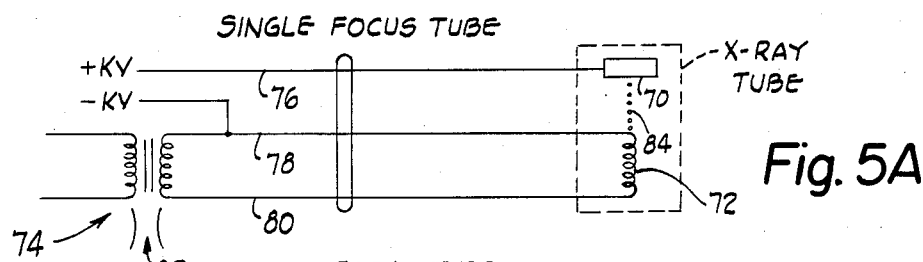
FIGS. 5A–5C show wiring schematics for high voltage energization of a CT X-ray tube.
Figure 5B:
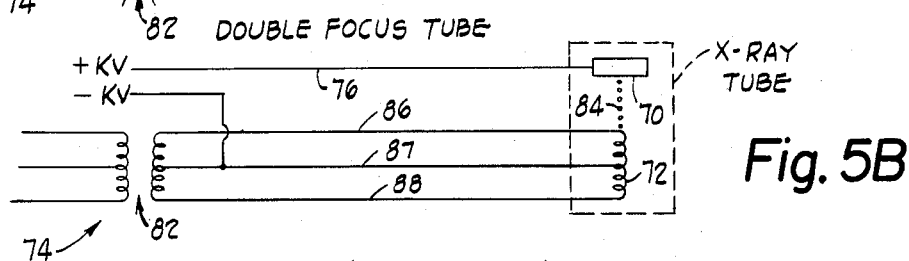
Figure 5C:
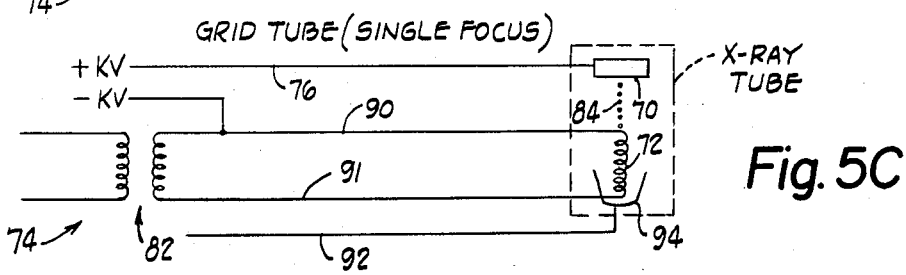

FIGS. 5A-C illustrate three different X-ray tube input configurations for energization of an X-ray tube. Each configuration shows an anode 70 and cathode 72 coupled to energization inputs. A series of these high voltage energization inputs 74 are shown transmitting potential differences to the tube.

In a single focus X-ray tube (See FIG. 5A) three high voltage inputs are needed. A first input 76 is the positive input to the X-ray anode and in the preferred embodiment of the invention is input through a first positive portion 56 of the slip ring arrangement. Two negative inputs 78, 80 are used to energize the cathode 72 and in the preferred embodiment are transmitted via the second portion 58 of the slip ring arrangement. A transformer 82 supplies a filament current which causes electrons 84 to be emitted thermionically from the cathode for acceleration towards the high potential anode 70.

FIG. 5B illustrates a double focus X-ray tube. Three negative high voltage inputs 86-88 are transmitted to the X-ray tube cathode 72. Through control of the voltages appearing on a primary of the transformer 82, it is possible to control the high voltage inputs 86-88 and provide a measure of X radiation control unavailable on the single focus tube.

An X-ray tube which includes a grid control is illustrated in FIG. 5C. This tube includes a high voltage positive input 76 and three high voltage negative inputs 90-92. Two inputs 90, 91 transmit a voltage appearing across the secondary of the transformer 82. A third input 92 serves to maintain a control voltage on a grid 94 within the X-ray tube. Through adjustment of grid tube potential a means of control over electron transmittal to the anode unavailable in the singly focus tube is provided.

From the illustrations in FIGS. 5A-5C it is apparent that a plurality of high voltage negative inputs must be available if single focus, double focus and grid X-ray tube control is to be achieved. The second negative portion 58 of the slip ring arrangement (See FIG. 3B) includes a plurality of slip rings for this purpose. In the preferred embodiment four slip rings are included to provide flexibility in CT scanner design. The voltage inputs to these slip rings are at many thousands of volts below ground but are each separated by relatively low voltages. In a single focus X-ray tube configuration, for example, the voltage separation between the two inputs 78, 80 need only be large enough to cause a filament current to flow in the X-ray tube cathode.

FIG. 4 shows a more detailed cross sectional view of the slip ring arrangement shown in FIG. 3B. That figure illustrates the X-ray tube housing 44, the rotating assembly 42 mounted by the bearing 64 inside the stationary gantry 40. The cross section depicted shows the frame 50 and one of its eight mounting connectors 43.

The FIG. 4 cross section shows the first positive 56 and second negative 58 slip ring portions noted with regard to FIG. 3B. The first portion sends a positive high voltage signal to the X-ray tube and the second portion includes 4 individual slip rings to provide the controlled energization of the cathode as mentioned above. Both the first 56 and second 58 portions of the slip ring arrangement are immersed in an oil bath in a cavity 112. This oil prevents arcing between high voltage portions of the slip ring arrangement and other portions of the CT apparatus which could damage both the control circuitry and the X-ray tube in prior art systems.

The portion of the stationary gantry 40 bordering on this cavity 112 is preferably of aluminum construction and the portion of the rotating assembly which borders the cavity is of a plastic construction. These light weight materials allow the apparatus to be readily tilted and the plastic rotating portions allow the system to be more easily rotated by the belt drive.

Four elastomeric seals 114-117 maintain a dielectric fluid such as oil in the cavity. These seals are mounted to the nonrotating gantry 40 and are biased against the rotating assembly by means of spring biasing members 118. As the assembly rotates with respect to the stationary gantry, these springs maintain the seals in contact with the rotating portions and thereby prevent leakage of the insulating fluid from the cavity 112.

The transmission path of the positive high voltage signal is clearly illustrated in FIG. 4. The high voltage signal (typically 75,000 volts) is input into the high voltage receptacle 46 transmitted to the first slip ring portion 56 then through high voltage cabling to a second high voltage receptacle 60 attached to the rotating assembly for transmittal to the anode portion of the X-ray tube. The high voltage passes through a brush which is biased towards the slip ring by a spring to insure contact between the brush and rotating slip ring. One type of cabling used to transmit the high voltages between the slip ring and the X-ray tube is Federal cabling which is known in the art of X-ray CT scanning. The cabling 120 passes through a bore machined into the plastic portion of the rotating assembly.

The second portion 58 of the slip ring assembly includes four rotating slip rings 122-125 which transmit four separate negative high voltage signals to the X-ray tube. A more detailed schematic of this second 58 portion of the slip ring arrangement is shown in FIG. 4A. As seen in that figure each rotating slip ring is contacted by a biased brush 127 which in turn is connected to an electrical contact in a housing 126. In the embodiment illustrated a single focus tube has been utilized and therefore only two negative high potential inputs 128, 129 are required with two spares available should other tubes be used.

At a location removed from the high voltage slip ring arrangement are a number of low voltage slip rings 130-135 for transmitting low voltage electrical signals from the stationary gantry to the rotating assembly. Since these slip rings transmit low voltages they need not be immersed in an oil bath to insure electrical isolation. Although only six slip rings are shown in the figure for clarity, 16 low voltage slip rings are utilized in a preferred embodiment of one commercial CT unit. Three of the low voltage inputs are utilized to provide power to a motor located in the rotating assembly 42 which cools the anode of the X-ray tube by rotating it. Three more of the low voltage slip rings are used as common or ground potential. Four other low voltage slip rings are utilized as general alternating current power inputs. These inputs are used to operate a number of solenoids mounted to the assembly 42 which must be powered by AC signals.

Five remaining slip rings are used to monitor and control the condition of three switches mounted to the rotating assembly which operate a shutter, a filter, and the collimator. The functioning of these three components must be coordinated with X-ray generation in the CT imaging process. One of these five remaining inputs transmits a frequency proportional to a reference intensity from the rotating assembly 42 to the stationary imaging electronics 20. Two of the remaining four inputs are used to provide synchronization and clock signals. The remaining two slip rings operate to send and receive digital data from a multiplexing board which both controls and monitors the condition of the three switches.

Since there are 16 rotating slip rings and the function of only 15 inputs have been described one of these 16 slip rings has no function in the present design but is available for future design modification.

While the embodiment described above has been characterized with some particularity, it should be appreciated to those skilled in the art that certain modification and changes could be incorporated without departing from the spirit or scope of the invention as detailed in the appended claims.

What is claimed is:

1. CT scanner apparatus comprising:
   (a) a gantry arrangement;
   (b) a rotatable assembly mounted on the gantry and defining a through patient aperture, said assembly including an x-radiation source;
   (c) a slip ring assembly around the aperture and having certain portions connected to the gantry and other portions forming a part of the rotating assembly for rotation relative to the certain portions, the slip ring assembly including at least one slip ring;
   (d) said other portions being electrically connected to the x-radiation source;
   (e) input means connected to the certain portions for receiving a high voltage electrical input and for transferring the electrical input to the source via the slip ring assembly;
   (f) drive means for rotating the rotatable assembly relative to the gantry;
   (g) said slip ring assembly being configured to provide a cavity for maintaining an insulating fluid in contact with substantially the entire slip ring as the slip ring portions rotate relatively; and,
   (h) further brushes and slip rings for low voltage connections to said rotatable assembly, said further brushes and slip rings being external of the cavity for insulating fluid and said further slip rings are concentrically disposed with respect to one another.

2. The apparatus of claim 1 wherein the slip ring assembly includes a plurality of axially aligned slip rings.

3. A computed tomographic system comprising:
   (a) a gantry delineating a patient receiving opening extending transversely therethrough;
   (b) a stationary housing structure connected to the gantry and including fixed end walls delineating the ends of a portion of a chamber, the fixed end walls terminating inwardly in circular surfaces;
   (c) a rotating housing structure telescoped within the stationary housing structure and including spaced movable end walls further defining such chamber, the movable end walls terminating radially outwardly in circular surfaces each of which is complemental to a fixed endwall surface;
   (d) spaced seals interposed between the complemental surfaces at each chamber end to effect a fluid seal between the housing structures and thereby provide a fluid tight chamber;
   (e) a single annular bearing interposed between the housing structures and supporting the rotating structure for rotation relative to the fixed housing structure about an axis extending through the patient opening;
   (f) an X-ray tube assembly carried by the rotating housing structure and including an X-ray tube adapted to emit a highly collimated, substantially planar spread beam along a path which intersects said axis;
   (g) a plurality of annular slip rings connected to a selected one of the fixed and rotating housing structures;
   (h) a plurality of high voltage slip ring brushes each electrically connected to an associated one of the slip rings to form a slip ring assembly and connected to the other of the fixed and rotating structures whereby each associated slip ring and brush are relatively rotated whenever the rotatable housing structure rotates, the slip rings and brushes being positioned within said chamber;
   (i) electrical connectors carried by the fixed housing structure for effecting electrical connections between the slip ring assemblies and electrical devices external of the fixed housing structure;
   (j) other electrical connectors carried by the rotating housing structure and effecting electrical connections between at least some of the slip ring assembly components and X-ray tube components;
   (k) a dielectric medium sufficiently filling said chamber to immerse the high voltage brush to slip ring connections; and
   (l) further slip ring assemblies having respective components respectively connected to the structures external of said cavity concentrically disposed with respect to one another.

4. The system of claim 3 wherein the annular slip rings are axially aligned.

5. A computed tomographic system comprising:
   (a) a gantry delineating a patient receiving opening extending transversely therethrough;
   (b) a stationary housing structure connected to the gantry and including walls delineating portions of a chamber, the walls terminating in circular surfaces;
   (c) a rotating housing structure coacting with the stationary housing structure and including spaced movable walls further defining such chamber, the movable walls terminating in circular surfaces each of which is complemental to a fixed endwall surface;
   (d) spaced seals interposed between the complemental surfaces to effect fluid seals between the housing structures and thereby provide a fluid tight chamber;
   (e) an annular bearing interposed between the housing structures and supporting the rotating structure for rotation relative to the fixed housing structure about an axis extending through the patient opening;
   (f) an X-ray tube assembly carried by the rotating housing structure and including an X-ray tube adapted to emit an X-ray beam along a path which intersects said axis;
   (g) a plurality of annular, high voltage slip rings each connected to a selected one of the fixed and rotating housing structures;
   (h) a plurality of high voltage slip ring brushes each electrically connected to an associated one of the slip rings to form a slip ring assembly and connected to the other of the fixed and rotating structures whereby each associated slip ring and brush are relatively rotated whenever the rotatable housing structure rotates, the slip rings and brushes being positioned within said chamber;
   (i) electrical connectors carried by the fixed housing structure for effecting electrical connections between the slip ring assemblies and electrical devices external of the fixed housing structure;

(j) other electrical connectors carried by the rotating housing structure and effecting electrical connections between at least some of the slip ring assembly components and X-ray tube components;

(k) a dielectric medium sufficiently filling said chamber to immerse the high voltage brush to slip ring connections; and (l) further slip ring assemblies having respective components respectively connected to the structures external of that part of the cavity that is filled with dielectric medium, said further slip rings are concentrically disposed with respect to one another.

6. The system of claim 5 wherein the high voltage slip rings are axially aligned.

7. CT scanner apparatus comprising:
(a) a gantry arrangement
(b) a rotatable assembly mounted on the gantry and defining a through patient aperture, said assembly including an x-radiation source;
(c) a slip ring assembly around the aperture and having certain portions connected to the gantry and other portions forming a part of the rotating assembly for rotation relative to the certain portions, the slip ring assembly including at least one slip ring;
(d) said other portions being electrically connected to the x-radiation source;
(e) input means connected to the certain portions for receiving a high voltage electrical input and for transferring the electrical input to the source via the slip ring assembly;
(f) drive means for rotating the rotatable assembly relative to the gantry;
(g) said slip ring assembly being configured to provide a cavity for maintaining an insulating fluid in contact with substantially the entire slip ring as the slip ring portions rotate relatively; and,
(h) further brushes and slip rings for low voltage connections to said rotatable assembly, said further brushes and slip rings being external of the cavity for insulating fluid;
(i) said further slip rings and the portions of the assembly defining said cavity are at least partially in concentric relationship to provide an apparatus of minimal axial length.

8. A computed tomographic system comprising:
(a) a gantry delineating a patient receiving opening extending transversely therethrough;
(b) a stationary housing structure connected to the gantry and including fixed end walls delineating the ends of a portion of a chamber, the fixed end walls terminating inwardly in circular surfaces;
(c) a rotating housing structure telescoped within the stationary housing structure and including spaced movable end walls further defining such chamber, the movable end walls terminating radially outwardly in circular surfaces each of which is complemental to a fixed endwall surface;
(d) spaced seals interposed between the complemental surfaces at each chamber end to effect a fluid seal between the housing structures and thereby provide a fluid tight chamber;
(e) a single annular bearing interposed between the housing structures and supporting the rotating structure for rotation relative to the fixed housing structure about an axis extending through the patient opening;
(f) an X-ray tube assembly carried by the rotating housing structure and including an X-ray tube adapted to emit a highly collimated, substantially planar spread beam along a path which intersects said axis;
(g) a plurality of annular slip rings connected to a selected one of the fixed and rotating housing structures;
(h) a plurality of high voltage slip ring brushes each electrically connected to an associated one of the slip rings to form a slip ring assembly and connected to the other of the fixed and rotating structures whereby each associated slip ring and brush are relatively rotated wherever the rotatable housing structure rotates, the slip rings and brushes being positioned within said chamber;
(i) electrical connectors carried by the fixed housing structure for effecting electrical connections between the slip ring assemblies and electrical devices external of the fixed housing structure;
(j) other electrical connectors carried by the rotating housing structure and effecting electrical connections between at least some of the slip ring assembly components and X-ray tube components;
(k) a dielectric medium sufficiently filling said chamber to immerse the high voltage brush to slip ring connections; and
(l) further slip ring assemblies having respective components respectively connected to the structures external of said cavity;
(m) said further slip rings and the portions of the structure defining said cavity are at least partially in concentric relationship to provide a system of minimal axial length.

9. A computed tomographic system comprising:
(a) a gantry delineating a patient receiving opening extending transversely therethrough;
(b) a stationary housing structure connected to the gantry and including walls delineating portions of a chamber, the walls terminating in circular surfaces;
(c) a rotating housing structure coacting with the stationary housing structure and including spaced movable walls further defining such chamber, the movable walls terminating in circular surfaces each of which is complemental to a fixed endwall surface;
(d) spaced seals interposed between the complemental surfaces to effect fluid seals between the housing structures and thereby provide a fluid tight chamber;
(e) an annular bearing interposed between the housing structures and supporting the rotating structure for rotation relative to the fixed housing structure about an axis extending through the patient opening;
(f) an X-ray tube assembly carried by the rotating housing structure and including an X-ray tube adapted to emit an X-ray beam along a path which intersects said axis;
(g) a plurality of annular, high voltage slip rings each connected to a selected one of the fixed and rotating housing structures;
(h) a plurality of high voltage slip ring brushes each electrically connected to an associated one of the slip rings to from a slip ring assembly and connected to the other of the fixed and rotating structures whereby each associated slip ring and brush are relatively rotated whenever the rotatable housing structure rotates, the slip rings and brushes being positioned within said chamber;

(i) electrical connectors carried by the fixed housing structure for effecting electrical connections between the slip ring assemblies and electrical devices external of the fixed housing structure;

(j) other electrical connectors carried by the rotating housing structure and effecting electrical connections between at least some of the slip ring assembly components and X-ray tube components;

(k) a dielectric medium sufficiently filling said chamber to immerse the high voltage brush to slip ring connections; and (l) further slip ring assemblies having respective components respectively connected to the structures external of that part of the cavity that is filled with dielectric medium;

(m) said further slip rings and the portions of the structures defining said cavity are at least partially in concentric relationship to provide a system of minimal axial length.

* * * * *